(12) United States Patent
Backensfeld et al.

(10) Patent No.: US 7,163,931 B2
(45) Date of Patent: Jan. 16, 2007

(54) COMPOSITIONS OF ESTROGEN-CYCLODEXTRIN COMPLEXES

(75) Inventors: Thomas Backensfeld, Berlin (DE); Wolfgang Heil, Berlin (DE); Ralph Lipp, Berlin (DE)

(73) Assignee: Schering Aktiengesellchaft, Berlin (DE)

( * ) Notice: Subject to any disclaimer, the term of this patent is extended or adjusted under 35 U.S.C. 154(b) by 73 days.

(21) Appl. No.: 11/102,681

(22) Filed: Apr. 11, 2005

(65) Prior Publication Data

US 2005/0182024 A1    Aug. 18, 2005

Related U.S. Application Data

(62) Division of application No. 10/022,845, filed on Dec. 20, 2001, now Pat. No. 6,958,326.

(60) Provisional application No. 60/256,484, filed on Dec. 20, 2000.

(30) Foreign Application Priority Data

Dec. 20, 2000 (EP) ................... 00610135

(51) Int. Cl.
  A01N 43/04 (2006.01)
  A61K 31/715 (2006.01)
  C08B 37/16 (2006.01)

(52) U.S. Cl. ............ 514/58; 514/23; 514/25; 514/54; 514/60; 536/103; 536/123.1; 536/124

(58) Field of Classification Search ............ 514/23, 514/25, 54, 58, 60; 536/103, 124, 123.1
See application file for complete search history.

(56) References Cited

U.S. PATENT DOCUMENTS

| 4,129,564 A | 12/1978 | Wiechert et al. |
| 4,154,820 A | 5/1979 | Simoons |
| 4,383,992 A | 5/1983 | Lipari |
| 4,596,795 A | 6/1986 | Pitha |
| 4,727,064 A | 2/1988 | Pitha |
| 4,877,774 A | 10/1989 | Pitha et al. |
| 5,376,641 A | 12/1994 | Ammeraal |
| 5,798,338 A | 8/1998 | Backensfeld et al. |
| 5,885,978 A | 3/1999 | Yamada et al. |
| 6,228,399 B1 | 5/2001 | Parikh et al. |
| 2005/0282790 A1 | 12/2005 | Nashed |

FOREIGN PATENT DOCUMENTS

| CA | 2016780 | 7/2000 |
| EP | 0 349 091 | 3/1990 |
| EP | 0 579 435 | 1/1994 |
| EP | 0398460 | 7/1997 |
| FR | 2515187 | 10/1982 |
| GB | 2109381 | 6/1983 |
| WO | WO 96/02277 | 2/1996 |
| WO | WO 96/09056 | 3/1996 |
| WO | WO 98/27929 | 7/1998 |
| WO | WO 00/21570 | 10/1999 |
| WO | WO 01/15701 | 3/2001 |

OTHER PUBLICATIONS

Rolf Krattenmacher, "Drospirenone: pharmacology and pharmacokinetics of a unique progestogen," *Contraception*, vol. 2, No. 1, Jul. 2000, pp. 29-38.
P. Norman, "Drospirenone: Contraceptive, Hormone Replacement Therapy, Aldosterone Antagonist, Progestogen: 1, 2-Dihydrospirorenone, SH-470, ZK-30595," *Drugs of the Future*, vol. 25, No. 12, Dec. 2000, pp. 1247-1256.
K. Uekama et al., "Inclusion of Complexations of Steroid Hormones With Cyclodextrins in Water and in Solid Phase," *International Journal of Pharmaceutics*, 10 (1982), pp. 1-15.
K. Králová et al., "Interactions of β-cyclodextrin with steroid compounds in aqueous solutions," *Pharmazie*, 1989, vol. 44, No. 9, pp. 623-625.
W.A.J.J. Hermens, "Delivery of hormones: some new concepts," *Pharm. Weekbl. Sci. Ed.*, 1992, vol. 14, No. 4 A, pp. 253-257.
K. Uekama, "Cyclodextrin Inclusion Compounds: Effects on Stability and Bio-Pharmaceutical Properties," *Topics in Pharmaceutical Sciences*, Eds. D.D. Breimer and P. Speiser, 1987, Elsevier Science Publishers (Biomedical Division), pp. 181-194.
K. Uekama et al., "Cyclodextrin Drug Carrier Systems," *Chem. Rev.*, vol. 98, No. 5, Jul. 1, 1998, pp. 2045-2076.
Pitha et al., "Hydroxypropyl-β-cyclodextrin: preparation and characterization; effects on solubility of drugs," *International Journal of Pharmaceutics*, 29(1), pp. 73-82 (1986).
European Search Report, Jun. 14, 2001.
Hafrun Fridriksdottir, design andin vivo testing of 17B-estradiol-HPBCD sublingual tablets, Die Pharmazie, Jan. 1996, pp. 39-42, No. 1, Eschborn, DE.
Thorsteinn Loftsson, The effect of water-soluble polymers on drug-cyclodextrin complexation, International Journal of Pharmaceutics, 1994, vol. 110, pp. 169-177.
Partial Eauropean Search Report dated Feb. 16, 2006 issued in EP 05 07 7665.
K. S. Parsey, et al., "An open-label multicenter study to evaluate Yasmin, a low-dose combination oral contraceptive containing drospirenone, a new progestogen", Elsevier Science Inc., (2000), pp. 105-111.
J. Huber, et al., "Efficacy and tolerability of a monophasic oral contraceptive containing ethinylestradiol and drospirenone", The European Journal of Contraception and Reproductive Health Care 2000, pp. 25-34.

*Primary Examiner*—Patrick Lewis

(57) ABSTRACT

Pharmaceutical compositions comprising low doses of sensitive complexes between an estrogen and a cyclodextrin are provided with improved stability. In specific embodiments the composition comprises a complex between ethinyl estradiol and β-cyclodextrin in a granulate preparation and in yet another embodiment the composition comprises a limited amount of polyvinylpyrrolidone since this excipient was found to degrade ethinyl estradiol. Furthermore, a method for improving the stability of an estrogen in a composition and for manufacturing such a stable composition is provided. Essentially, the granulate preparation are manufactured under careful control of the relative humidity.

52 Claims, No Drawings

COMPOSITIONS OF ESTROGEN-CYCLODEXTRIN COMPLEXES

This application is a divisional of U.S. Ser. No. 10/022,845, filed Dec. 20, 2001 now U.S. Pat. No. 6,958,326.

This application claims priority to U.S. Provisional Application No. 60/256,484, filed Dec. 20, 2000.

FIELD OF INVENTION

The present invention relates to pharmaceutical compositions and formulations comprising a cyclodextrin-estrogen complex that confers very high chemical stability to the estrogen. The invention allows for an improved physical stability of cyclodextrin-estrogen complexes and of the chemical stability of estrogens such ethinyl estradiol upon storage.

BACKGROUND OF THE INVENTION

Degradation of estrogens, such as ethinyl estradiol, in conventional pharmaceutical products is one of the most critical issues with regard to product shelf life. Stabilization of the estrogen may be achieved by either product packaging in hermetic containers or, more effectively, as in the present invention, by actual stabilization of the pharmaceutical product.

Pharmaceutical products comprising naturally or synthetically derived sex hormones often consist of low dosages of these active ingredients. Given the small amounts of active ingredient required per single dosage, often ranging between 0.1 µg and 500 µg, it is problematic to manufacture unit dosage formulations with reliably consistent amounts of active agent which do not fluctuate within one batch or between batches. Thus, the requirements of content uniformity as set forth by health authorities may not be met.

Moreover, degradation of these small amounts of active ingredient is a further contributor to the fluctuations of the active ingredient in low dosage formulations.

In general, these low dose formulations comprising unstable active agents are problematic in terms of their preparation, storage and use, and there is a need for providing means for stabilization of such formulations.

Complexation of estrogens with cyclodextrins is widely used for improving stability, solubility or bioavailability. For example, EP 0 349 091 discloses compositions containing complexes between 17-β-estradiol and dimethyl-β-cyclodextrin for improving nasal administration, Fridriksdottir et al (Die Pharmazie, vol. 51, 1996, pages 39–42) describes complexes between cyclodextrin and 17-β-estradiol for improving the solubility in aqueous solution so as to improve sublinqual application. Improved solubility is also the focus of U.S. Pat. No. 4,596,795, which relates to a complex between α-, β- and γ-cyclodextrins and derivatives thereof with testosterone, progesterone, and estradiol. U.S. Pat. No. 4,383,992 discloses a water soluble inclusion compound formed by complexing a steroid compound, such as an estrogen with beta-cyclodextrin.

Moreover, U.S. Pat. No. 5,798,338 discloses that the oxidative degradation of 17-α-ethinyl estradiol is reduced upon forming clathrates (complexes) between β-cyclodextrin and 17-α-ethinyl estradiol.

However, although complexation of estrogens with cyclodextrins may solve critical issues with regards to solubility, bioavailability and stability, there are still further problems to solve before complexes between active agents, such as estrogens, and cyclodextrins are suitable for use in pharmaceutical products. Namely, the complexes are prone to dissociation into the free estrogen and the cyclodextrin, particularly upon contact with water. The lack of physical stability of cyclodextrin-estrogen complexes results in significant amounts of free estrogen present in compositions due to, for instance, exposure to aqueous media during the manufacturing process, particularly during granulation. As a consequence, the lifetime of the composition may be decreased due to degradation of free estrogen.

Moreover, the intended improved bioavailability sought by complexing estrogen with cyclodextrin is not achieved due to the lack of physical stability of the cyclodextrin-estrogen complex and the chemical instability of the free estrogen.

Various attempts have been made in order to stabilize compositions comprising complexes between a cyclodextrin and an estrogen. For example, the composition may be stabilized by stabilizing the complex itself. Thus, U.S. Pat. No. 4,727,064 attempts the stabilization of complexes upon using amorphous forms of the complex. Alternatively, complexes may be stabilized and their solubility increased upon adding polymers to the reaction medium upon complexation, as disclosed by Loftsson et al. (Int. J. Pharmaceutics, Vol. 110, 1994, pp 169–177). EP 0579435 also discloses complexes between estradiol and cyclodextrins wherein the addition of polymers to the reaction medium increases the stability constant of the complex.

The compositions may also be stabilized upon avoiding a granulation step in the manufacturing process of the composition, as disclosed in WO 00/21570.

There is a need in the art for processes for preparing physically stable complexes of cyclodextrin and estrogen and for compositions, which improve the stability of both the complex and the free estrogen. There is furthermore a need in the art for granulate formulations which allow for physically stable cyclodextrin-estrogen complexes.

SUMMARY OF THE INVENTION

An object of the present invention is to provide a stable and homogenous pharmaceutical product comprising an estrogen, wherein the stability of the estrogen is significantly improved over that of conventional products, which have complexed estrogens or sensitive complexes between a cyclodextrin and an estrogen. Degradation of estrogens, such as ethinyl estradiol, in conventional products, is one of the most critical issues with regard to product shelf life.

It has surprisingly been found that products with improved stability of the estrogen are achieved by means of complexing estrogen with cyclodextrins, the judicious selection of excipients and/or proper adaptation of the manufacturing process. Consequently, the shelf-life of an estrogen-containing product is improved.

Thus, an important aspect of the invention relates to formulations and compositions comprising complexes between an estrogen and a cyclodextrin that are stable in spite of being manufactured by granulation. That is to say that the invention relates in a first aspect to a formulation comprising a complex between an estrogen and a cyclodextrin, wherein the formulation is a granulate preparation, said granulation preparation having a relative humidity of at most 60%, as determined at a temperature between 20° C. and 40° C.

In a further aspect, the invention relates to compositions comprising i) a complex between an estrogen and a cyclodextrin; and ii) one or more excipient(s), the composition having a stability such that said estrogen is in amount of at least 85% w/w in relation to the initial content of the estrogen after storage for 12 months at 40° C. and 75% relative humidity (RH). In a suitable embodiment thereof, the composition comprises a granulate preparation comprising said complex. In a further suitable embodiment, the composition is compressed directly into a tablet or equivalent unit dosage forms. Upon further study of the specification and appended claims, further aspects and advantages of this invention will become apparent to those skilled in the art.

Thus, contrarily to previous findings, it is possible to obtain stable compositions comprising an estrogen-cyclodextrin-complex in a granulate preparation.

Compositions of the present invention may be used as medicaments. Accordingly, the use of a composition described infra for the preparation of a medicament for female contraception, for hormone replacement therapy, or for treating acne or PMDD (pre-menstrual dysfunction disorders), is a further aspect of the present invention.

In a broad sense, the present invention relates to a method of improving the stability of an estrogen in a pharmaceutical composition that comprises an estrogen-cyclodextrin complex and one or more excipients in a granulate preparation, the method comprises the steps of:
i) forming a complex between said estrogen and a cyclodextrin; and
ii) mixing under granulation conditions the said complex with the one or more excipients such that the relative humidity of the final granulate does not exceed 60%, as determined at a temperature between 20° C. and 40° C.

Finally, the invention relates to a process for manufacturing a composition comprising a granulate preparation of a complex between an estrogen and a cyclodextrin, wherein the processing of the granulate preparation comprises the steps of
i) loading the complex, one or more excipients and optionally one or more therapeutically active agent(s) into a granulator;
ii) applying a liquid onto the loaded complex and the one or more excipients under granulation conditions so as to obtain granules having a relative humidity not exceeding 60%, as determined at a temperature between 20° C. and 40° C.

DETAILED DESCRIPTION OF THE INVENTION

The term "complex" is intended to mean a complex between an estrogen and a cyclodextrin, wherein a molecule of said estrogen is at least partially inserted into the cavity of one cyclodextrin molecule. Furthermore, the molecule of an estrogen may at least partially be inserted into the cavity of more cyclodextrin molecules, and two moieties of a single estrogen molecule may each be inserted into one cyclodextrin molecule to give 2:1 ratio between cyclodextrin and estrogen. Thus, the complex may be termed as an inclusion complex (clathrate) between an estrogen and a cyclodextrin. Similarly, the complex may comprise more than one molecule of estrogen at least partially inserted into one or more cyclodextrin molecules, wherein for example 2 estrogen molecules are at least partially inserted into a single cyclodextrin molecule, to give a 1:2 ratio between cyclodextrin and estrogen. Complexes wherein one estrogen molecule is complexed with one or more cyclodextrin molecules are certainly anticipated such as 1 estrogen molecule complexed with 2 cyclodextrin molecules or 3 cyclodextrin molecules. Typically, the ethinyl estradiol-β-cyclodextrin complex as prepared by the present invention is preferably a complex between one molecule of ethinyl estradiol and two molecules of β-Cyclodextrin. The term "ethinyl estradiol-β-Cyclodextrin complex" or "EE-β-CD" is intended to mean a complex, of any ratio, between ethinyl estradiol and β-cyclodextrin.

The term "granulate preparation" relates to a preparation of a powder, wherein the particle size of the powder is either increased upon processing with a liquid or by compression. The liquid may be of any kind of aqueous or organic solvents, or mixtures thereof, optionally further comprising a binder such as a starch. Thus, a "granulate preparation" relates in a broad sense to granules, pellets and compressed powder or any particle formed by granulation, pelletation or compression of powder such that a mean particle size of at least about 100 μm are formed.

The term "cyclodextrin" is intended to mean a cyclodextrin or a derivative thereof as well as mixtures of various cyclodextrins, mixtures of various derivatives of cyclodextrins and mixtures of various cyclodextrins and their derivatives. The cyclodextrin is further defined according to the invention.

The present inventors have developed products, wherein a remarkable improvement of the stability of an estrogen has been achieved by combined means. One such means is by the protection of the estrogen by forming a cyclodextrin complex. Another such means is by the judicious adaptation of the granulation process such that e.g. the dissociation of the complex into free estrogen and cyclodextrin is restricted during the manufacturing of the granulate preparation. The present inventors have provided data indicating that a complex between ethinyl estradiol and β-cyclodextrin is poorly stable when exposed to water. Actually, in the event where the complex is dissolved in water, about 50% of the complex are dissociated into free ethinyl estradiol and cyclodextrin within 3 minutes (see Example 6 herein). Thus, without being limited to a particular theory, the stability of the products is, at least in part, improved by limiting the dissociation of the complex into free estrogen during the manufacturing process, thereby limiting the content of free estrogen in the final product.

Therefore, in a first aspect the invention relates to a formulation comprising a complex between an estrogen and a cyclodextrin, wherein the formulation is a granulate preparation, said granulation preparation having a relative humidity of at most 60%, as determined at a temperature between 20° C. and 40° C. Preferably, the relative humidity is at most 55%, preferably of at most 45%, most preferably of at most 40%, as determined at a temperature between 20° C. and 40° C.

As stated, the present invention has lead to stable products comprising sensitive complexes between an estrogen and a cyclodextrin. Thus, in a second aspect, the invention relates to a composition comprising:
i) a complex between an estrogen and a cyclodextrin; and
ii) one or more excipient(s), the composition having a stability such that said estrogen is in an amount of at least 85% w/w in relation to the initial content of the estrogen after storage for 12 months at 40° C. and 75% relative humidity (RH). The initial content of estrogen should be understood as the weighed quantity of estrogen included in the composition upon manufacturing the final formulation.

In one embodiment hereof, the composition is in a form of a tablet manufactured by direct compression of the composition. Preferably the composition comprises a restricted amount of polyvinylpyrrolidone as disclosed further herein.

In yet another embodiment, the complex between an estrogen and a cyclodextrin is formulated into the granulate preparation as defined herein.

In preferred embodiments, the composition has a stability such that said estrogen is in an amount of at least 90% w/w, more preferably of at least 95% w/w, most preferably of at least 97% w/w such as of at least 98% in relation to the initial content of the estrogen after storage for 12 months at 40° C. and 75% relative humidity (RH).

One further means for improving the stability of an estrogen in such formulations and compositions comprises the judicious selection of excipients such that the content of excipients capable of inducing degradation of ethinyl estradiol are minimised or excluded from the formulations. One such critical excipient is polyvinylpyrrolidone, which is typically used as a binding agent for fluid bed granulation. As disclosed herein, the ethinyl estradiol is sensitive to polyvinylpyrrolidone and significant quantities of ethinyl estradiol is degraded in formulations and compositions, nonetheless the ethinyl estradiol is protected in the form of a clathrate. For example, compositions comprising polyvinylpyrrolidone and prepared as disclosed in Example 3 of U.S. Pat. No. 5,798,338, by fluid bed granulation have a poor stability with respect to ethinyl estradiol. The present inventors has found that in such a composition the content of ethinyl estradiol is decreased by 25% in relation to the initial content of the ethinyl estradiol after storage for 12 months at 40° C. and 75% relative humidity (See table 1.4, Example 1, Table A). Therefore, one aspect of the invention relates to compositions/formulations low in the content of compounds with relatively high oxidising potential such as an oxidising potential greater than or similar to polyvinylpyrrolidone. For example, the compositions/formulations of the present invention preferably have less polyvinylpyrrolidone than the compositions of Example 3 of U.S. Pat. No. 5,798,338. More preferably, suitable embodiments of the invention relate to compositions/formulations comprising at most 2% w/w of polyvinylpyrrolidone, preferably at most 1% w/w, more preferably at most 0.5% w/w, most preferably at most 0.2% w/w of polyvinylpyrrolidone. Moreover, particular interesting embodiments relate to compositions/formulations essentially free of polyvinylpyrrolidone.

Individually, or acting in concert, the above mentioned means have resulted in compositions, wherein the estrogen is more stable than in conventional compositions comprising polyvinylpyrrolidone that are manufactured by direct compression or by an improper fluid bed granulation process. The thus provided stable compositions is characterised by having a content of said estrogen of at least 90% w/w in relation to the initial content of said estrogen after storage for 3 months at 40° C. and 75% relative humidity (RH). Preferably, the content of said estrogen is least 92% w/w, more preferably at least 94% w/w, even more preferably at least 96% w/w and most preferably at least 98% w/w in relation to the initial content of estrogen after storage for 3 months at 40° C. and 75% relative humidity (RH).

Likewise, the compositions are also stable at higher temperatures, e.g. at 60° C. and 75% relative humidity, wherein the stability is such that a content of estrogen, as determined after 3 months storage at 60° C. and 75% relative humidity (RH), is 85% w/w in relation to the initial content of said estrogen, preferably at least 90% w/w, more preferably at least 92% w/w, even more preferably at least 94% w/w, most preferably at least 96% w/w in relation to the initial content of said estrogen.

Importantly, the compositions according to the invention are more stable at ambient conditions in comparison to conventional compositions. Thus, the compositions as disclosed herein have improved stability upon storage for 12 months at 25° C. and 60% relative humidity (RH), such that said estrogen is in an amount of at least 95% w/w in relation to the initial content of said estrogen. Preferably, the content of estrogen is at least 96% w/w, more preferably at least 97% w/w, most preferably at least 98% w/w in relation to the initial content of estrogen after storage for 12 months at 25° C. and 60% relative humidity (RH).

As the person skilled in the art will appreciate, the estrogen may be selected from the group consisting of ethinyl estradiol (EE), estradiol, estradiol sulfamates, estradiol valerate, estradiol benzoate, estrone, estriol, estriol succinate and conjugated estrogens, including conjugated equine estrogens such as estrone sulfate, 17β-estradiol sulfate, 17α-estradiol sulfate, equilin sulfate, 17β-dihydroequilin sulfate, 17α-dihydroequilin sulfate, equilenin sulfate, 17β-dihydroequilenin sulfate and 17α-dihydroequilenin sulfate or mixtures thereof. Particular interesting estrogens are selected from the group consisting of ethinyl estradiol (EE), estradiol sulfamates, estradiol valerate, estradiol benzoate, estrone, and estrone sulfate or mixtures thereof, notably ethinyl estradiol (EE), estradiol valerate, estradiol benzoate and estradiol sulfamates. Most preferred is ethinyl estradiol (EE).

In the preferred embodiment wherein the estrogen is ethinyl estradiol (EE), some of the degradation products are well known. Thus, unstable compositions, e.g. those comprising a sensitive complex between an ethinyl estradiol and a cyclodextrin that are manufactured by said conventional granulation methods, comprises degradation products of ethinyl estradiol, in particular following storage for a period of time. Moreover, since more ethinyl estradiol is degraded in said conventional compositions than in those developed by the present inventors (see Example 2, table 1.3), the conventional compositions may comprise higher quantities of these degradation products.

Accordingly, the stability according to one embodiment of the present invention is such that a molar sum product of known degradation products of ethinyl estradiol is at most 0.8% in relation to the initial content of ethinyl estradiol. Thus, wherein the estrogen is ethinyl estradiol, the molar sum product of 6-α-hydroxy-ethinyl estradiol, 6-β-hydroxy-ethinyl estradiol, 6-keto-ethinyl estradiol, Δ6,7-ethinyl estradiol and Δ-9,11-ethinyl estradiol totals at the most 0.8% in relation to the initial molar content of ethinyl estradiol as determined after storage for 12 months at 25° C. and 60% relative humidity (RH). Preferably, the molar sum product totals at the most 0.7% and more preferably at the most 0.6% at these storage conditions.

Furthermore, the stability is such that a molar sum product 6-α-hydroxy-ethinyl estradiol, 6-β-hydroxy-ethinyl estradiol, 6-keto-ethinyl estradiol, Δ6,7-ethinyl estradiol and Δ-9,11-ethinyl estradiol, totals at the most 3% in relation to the initial molar content of ethinyl estradiol as determined after storage for 12 months at 40° C. and 75% relative humidity (RH). Preferably, the molar sum product totals at most 2% and more preferably at the most 0.6% at those storage conditions.

As stated, an object of the present invention is to provide a pharmaceutical composition/pharmaceutical formulation comprising a complex between an estrogen and cyclodextrin, wherein the stability of said estrogen is significantly improved over that of conventional compositions/formulations. Thus, for further improving the stability or ensuring the stability of embodiments according to the invention, the composition/formulations further comprises an antioxidant. The antioxidant may either be included in the granulate preparation or added to the composition as a further excipient.

The cyclodextrin may be selected from α-cyclodextrin, β-cyclodextrin, γ-cyclodextrin and derivatives thereof. The cyclodextrin may be modified such that some or all of the primary or secondary hydroxyls of the macrocycle, or both, may be alkylated or acylated. Methods of modifying these alcohols are well known to the person skilled in the art and many are commercially available. Thus, some or all of the hydroxyls of cyclodextrin may modified cyclodextrins have be substituted with an O—R group or an O—C(O)—R, wherein R is an optionally substituted $C_{1-6}$ alkyl, an optionally substituted $C_{2-6}$ alkenyl, an optionally substituted $C_{2-6}$ alkynyl, an optionally substituted aryl or heteroaryl group. Thus, R may be methyl, ethyl, propyl, butyl, pentyl, or hexyl group. Consequently, O—C(O)—R may be an acetate. Furthermore, with the commonly employed 2-hydroxyethyl group, or 2-hydroxypropyl group R may be used to derivatize cyclodextrin. Moreover, the cyclodextrin alcohols may be per-benzylated, per-benzoylated, or benzylated or benzoylated on just one face of the macrocycle, or wherein only 1, 2, 3, 4, 5, or 6 hydroxyls are benzylated or benzoylated. Naturally, the cyclodextrin alcohols may be per-alkylated or per-acylated such as per-methylated or per-acetylated, or alkylated or acylated, such as methylated or acetylated, on just one face of the macrocycle, or wherein only 1, 2, 3, 4, 5, or 6 hydroxyls are alkylated or acylated, such as methylated or acetylated.

The estrogen-cyclodextrin complex may be obtained by methods known to the person skilled in the art (e.g. U.S. Pat. No. 5,798,338).

The ethinyl estradiol-β-cyclodextrin complex may also be obtained by co-precipitation as follows: Ethinyl estradiol is dissolved in ethanol; β-cyclodextrin is dissolved at 45° C. in water; the ethinyl estradiol solution is added to the beta-cyclodextrin solution; the obtained suspension is stirred for some hours at 20 to 25° C. and afterwards at 2° C.; the crystallisation product is isolated and dried.

Alternatively, the ethinyl estradiol-β-cyclodextrin complex may be obtained as follows: Ethinyl estradiol is dissolved in acetone; β-cyclodextrin is dissolved at 45° C. in water; the ethinyl estradiol solution is added to the β-cyclodextrin solution; the obtained suspension is stirred for some hours at temperatures below 25° C.; afterwards, the crystallisation product is isolated and dried.

Preferably, the complex between a cyclodextrin and an estrogen may have a given lipophilicity (hydrophobicity). Thus, suitable embodiments according to the invention relates to those, wherein the complex has a n-octanol/water partition coefficient of the complex at pH 7 ranging from about 2 to 5, preferably from about 3 to 4. Further interesting embodiments comprises the complex in crystalline form. Thus, in a limited aspect, the invention relates to crystalline complexes between an estrogen and a cyclodextrin. The term "crystalline" relates to various modifications of the physical structure of a compound, wherein a part of the compound can be in amorphous form. Crystalline compounds may be characterised by being hydrated and containment of crystal water. Finally, the complexes may be defined by the examples provided herein such as those hydrated complexes disclosed in Example 12. Moreover, the crystalline complex may contain parts of free ethinyl estradiol and free cyclodextrin.

Preferably, the complex comprises of β-cyclodextrin or a derivative thereof, most preferably β-cyclodextrin. Thus, in a particularly preferred embodiment of the invention, which is a combination of preferred embodiments, the estrogen is ethinyl estradiol and the cyclodextrin is β-cyclodextrin.

In an alternative embodiment of the invention, the composition further comprises one or more therapeutically active agent. Thus, in this embodiment, the composition further comprises a progestogen. The progestogen may be selected from the group consisting of drospirenone, levonorgestrel, norgestrel, gestodene, dienogest, cyproterone acetate, norethisterone, norethisterone acetate, desorgestrel, 3-keto-desorgestrel. However, the preferred progestogen is drospirenone.

In the preferred embodiment wherein the therapeutically active substance is drospirenone, said drospirenone may optionally be micronized. In the preferred embodiment where the therapeutically active substance is drospirenone, all or substantially all of said drospirenone may be present as a complex with cyclodextrin. As the person skilled in the art will appreciate, the dissociation of the drospirenone cyclodextrin complex may result in a mixture of cyclodextrin-complexed drospirenone and uncomplexed (free) drospirenone. As was the case for uncomplexed drospirenone, the complexed drospirenone may also be micronized.

Thus, a preferred embodiment of the invention relates to a composition/formulation wherein the estrogen is ethinyl estradiol and the one or more therapeutically active agent(s) is drospirenone. A further interesting embodiment in connection hereto is where both the estrogen-cyclodextrin complex and the drospirenone are micronized.

As stated, the compositions and formulations comprises low doses of active agent, such that typical embodiments according to the invention comprises estrogen in an amount corresponding to a therapeutically equivalent amount of ethinyl estradiol of from about 0.002% w/w to 2% w/w.

In yet other typical embodiments, the composition/formulations comprises the estrogen, ethinyl estradiol, in an amount from about 0.002% w/w to 2% w/w. Preferably, the amount is from about 0.004% w/w to 0.2% w/w, more preferably from about 0.008% w/w to 0.1% w/w, most preferably from about 0.02% w/w to 0.05% w/w.

When taking the amount of the cyclodextrin into account such as in preferred embodiments wherein the estrogen is ethinyl estradiol and the cyclodextrin is β-cyclodextrin, the ethinyl estradiol is in an amount relative to the ethinyl-estradiol-β-cyclodextrin complex of from about 5% w/w to 20% w/w, preferably from about 8% w/w to 15% w/w, most preferably from about 9% w/w to 13% w/w.

Furthermore, according to the invention, the ratio between the estrogen and the cyclodextrin may be adjusted. Therefore, in suitable embodiments, the estrogen is in an amount relative to the cyclodextrin such that a molar ratio between the estrogen and the cyclodextrin is from about 2:1 to 1:10, preferably from about 1:1 to 1:5, most preferably from about 1:1 to 1:3, such as 1:1 and 1:2.

In embodiments wherein the composition further comprises a therapeutically active compound and that said compound is drospirenone, the drospirenone is in an amount from about 0.4% to 20% w/w, preferably from about 0.8% w/w to 10% w/w, more preferably from about 1.5% w/w to 5% w/w.

A further object of the invention is to provide a composition Or a formulation as described herein further formulated as a unit dosage form, preferably such as a tablet, capsule or sachets.

A typical embodiment of the invention relates to a composition or a formulation in form of granules, pellets or dry compressed blends that may be filled into hard gelatine capsules or sachets, or compressed into tablet cores. In that event, the composition or formulation comprises (% wt/wt):

i) Active agent: complex between ethinyl estradiol arid β-cyclodextrins;
ii) 0–95% w/w of filling agents such as lactose, starch, cellulose and/or others;
iii) 0–15% w/w of binding agents such as starch, cellulose, hydroxypropylcellulose hydroxypropylmethylcellulose, maltodextrine and/or others;
iv) 0–5% w/w of glidants such as colloidal silicon dioxide and/or others;
v) 0–15% w/w of disintegrating agents such as starch, carmellose-calcium, crosscarmellose-sodium, carboxymethylstarch sodium and/or others;
vi) 0–5% w/w of stabilizers/antioxidants such as tocopherole acetate, propyl gallate, ascorbic acid, ascorbic palmitate and/or others; and
vii) 0–5% w/w of lubricants such as magnesium stearate and/or others.

In the embodiment wherein the composition/formulation further comprises a therapeutically active compound, such as a progestogen, preferably drospirenone, a typical formulation may further comprise 0.1–15% w/w of drospirenone.

A particular interesting embodiment relates to a unit dosage form comprising:

| | |
|---|---|
| Drospirenone (micronized) | 3.00 mg |
| Ethinyl estradiol as β-cyclodextrin clathrate (micronized) | 0.02 mg* |
| Lactose | 48.18 mg** |
| Corn starch | 28.00 mg |
| Magnesium stearate | 0.8 mg |
| Water | (processing aid) |

*0.02 is the concentration of ethinyl estradiol (not taken β-cyclodextrin into consideration). The amount of ethinyl estradiol in the β-cyclodextrin clathrate is 9.5 to 12.5%.
**the amount of lactose is to be adjusted to the amount of β-cyclodextrin.

A further aspect of the invention relates to a method for improving the stability of an estrogen in a pharmaceutical composition that comprises an estrogen and one or more excipients in a granulate preparation, the method comprises the steps of:
i) forming an complex between said estrogen and a cyclodextrin; and
ii) mixing under granulation conditions the said complex with the one or more excipients such that the relative humidity of the final granulate does not exceed 60%, as determined at a temperature between 20° C. and 40° C.

As described herein, this method of stabilizing results in compositions that are more stable than reported for conventional compositions. The important features leading to the improved stability relates, at least in part, to the granulation process and to the proper choice of excipients. Thus, the method of improving the stability relates to the proper adjusting of the relative humidity of the granulate preparation. Most importantly, the relative humidity may not exceed 60% relative humidity, as determined at a temperature between 20° C. and 40° C. Preferably, the relative humidity does not exceed 55%, more preferably does not exceed 45%, most preferably does not exceed 40%, as determined at a temperature between 20° C. and 40° C.

In a further related aspect hereof, the invention relates to a method for improving the stability of an estrogen in a pharmaceutical composition that comprises an estrogen and one or more excipients, the method comprises the steps of:
i) forming an complex between said estrogen and a cyclodextrin; and
ii) adding excipients in an amount so as to minimise the overall amount of excipients which have an oxidising potential greater than or similar to polyvinylpyrrolidone.

The aim is to restrict or minimise the amount of excipients, which have oxidising potentials greater than or similar to polyvinylpyrrolidone.

Thus, the method of stabilizing also relates to limiting the content of excipients with an oxidising potential greater than or similar to polyvinylpyrrolidone, including limiting the content of polyvinylpyrrolidone in the compositions/formulations. Thus, interesting embodiments of the invention relate to those wherein the one or more excipient(s) comprises polyvinylpyrrolidone in an amount of at most 2% w/w. Preferably, the amount is at most 1% w/w, more preferably at most 0.5% w/w, most preferably at most 0.2% w/w. In a very preferred embodiment, the method of improving stability relates to excluding polyvinylpyrrolidone from the pharmaceutical composition. Thus, a method of stabilizing an estrogen in a pharmaceutical composition relates to a composition/formulation essentially free of polyvinylpyrrolidone.

A still further object of the invention is to provide a process for preparing compositions and formulations that are stable and homogenous and as described supra. Suitable process conditions comprise the steps of preparing a granulation liquid, individually loading the active agents and the one or more excipient(s) into equipment suitable for granulation, granulating and drying. In a preferred embodiment hereof, the thus obtained granules have a relative humidity of at most 60%.

Thus, the invention relates to a process for manufacturing a granulate preparation comprising a complex between an estrogen and a cyclodextrin, wherein the processing of the granulate preparation comprises the steps of:
i) loading the complex and one or more excipients into a granulator;
ii) applying a liquid onto the loaded complex and the one or more excipients under granulation conditions so as to obtain granules having a relative humidity not exceeding 60%, as determined at a temperature between 20° C. and 40° C.

The process has lead to novel compositions comprising less degraded estrogen and less degradation products in comparison to those compositions manufactured by conventional processes such as those granulation techniques using polyvinylpyrrolidone and/or techniques wherein the relative humidity are not properly adjusted.

Thus, in preferred embodiments according to the invention, the granulation conditions are even more restricted such as the relative humidity of the granulate preparation does not exceed 55%, preferably does not exceed 45%, most preferably does not exceed 40%, as determined at a temperature between 20° C. and 40° C. Furthermore, the amount of polyvinylpyrrolidone is restricted.

As stated, the formulation comprises low doses of the active agents, in particularly of the ethinyl-estradiol-cyclodextrin complex. Consequently, it is critical to achieve homogenous formulations and to meet the requirements of content uniformity. Thus, an important issue to consider, when manufacturing compositions/formulations containing low doses of the active ingredient, is the homogeneity of the granulate preparation. Common practice applies to the use of pre-mixes of the active ingredient with an excipient, e.g. lactose when manufacturing low-dosages formulations. The pre-mix is normally made in a separate blending step. However, the present inventors have developed a process for manufacturing low-dosage formulations without using a step of pre-mixing the active agent with a suitable excipient.

Thus, an interesting embodiment of the invention relates to a method as described supra wherein the complex and the optionally further one or more therapeutically active agent (s) are provided as individual agent(s) without being pre-mixed with excipients. In a further embodiment related hereto, one or more therapeutically active agent(s), such as drospirenone, is further added to the granulator.

As stated, the properly adapted process of the invention has lead to the manufacturing of homogenous batches of the granulate preparation. In the event where the process further lead to unit dosage forms, such as a tablet, content uniformity is achieved. Thus, in very suitable embodiments of the invention, batches of final granulate and/or final unit dosage forms comply with the content uniformity so as to be within the range of 85% and 115%, preferably within the range of 90% and 110%, more preferably within 95% and 115%. The content uniformity is determined by taking 10 random samples of the granulate preparation or by randomly taken 10 tablets from a batch of tablets, determining the quantitative content of estrogen in each sample or tablet, and finally calculating the coefficient of variation based on the individual quantities of estrogen.

The low doses referred to in this context relate to compositions/formulations comprising the complex in an amount of from about 0.005% w/w to 20% w/w, preferably from about 0.01% w/w to 2% w/w, more preferably from about 0.05% w/w to 1% w/w, even more preferably from about 0.1% w/w to 0.7% w/w, most preferably from about 0.15% w/w to 0.5% w/w.

The granulation may be provided by any equipment that will provide a stable and homogenous granulate according to the invention. That is to say any equipment suitable for obtaining granules having a relative humidity of at most 60% at temperatures from 20° C. to 40° C. However, in a preferred embodiment, the granulation conditions are provided by fluidised bed granulation.

A further object of the invention is related to the use of compositions described herein and in the Examples in the preparation of a medicament for female contraception, for hormone replacement therapy, or for treating acne or PMDD (pre-menstrual dysfunction disorder).

The use of a compound of the present invention for hormone replacement therapy relates to treating menopausal, pre-menopausal, and/or post-menopausal symptoms in a female. The medicament is suitably formulated according to general knowledge for a person skilled in the pharmaceutical art typically for oral administration.

In a preferred embodiment, the medicament is suitable for inhibiting ovulation in a female. Apart from its ability to inhibit ovulation, the composition of the invention has been found to possess pronounced anti-androgenic properties and may therefore be used in the prevention or treatment of androgen-induced disorders, in particular acne. Such use may be independent from or concomitant with the use as a contraceptive disclosed above. Furthermore, since drospirenone is an aldosterone antagonist, it has diuretic properties and is therefore suitable for counteracting the water-retentive properties of ethinyl estradiol.

As stated, the use of compositions for the preparation of a medicament for oral administration, preferably comprises the use of compositions comprising a complex between ethinyl estradiol and β-cyclodextrin and further comprising a therapeutically active agent. Most preferably, the agent is drospirenone. In a combination of preferred embodiments, the dose of ethinyl estradiol is from 0.015 mg to 0.04 mg, in particular from about 0.015 mg to 0.03 mg, and the dose of drospirenone is from about 2.5 mg to 3.5 mg, in particular about 3 mg for a daily dosage unit. More particularly, the compositions of the invention comprise an amount of drospirenone corresponding to a daily dosage of from about 3.0 to 3.5 mg and ethinyl estradiol in an amount corresponding to from about 0.015 to 0.03 mg.

The medicament for use in inhibiting ovulation may be an one-phase composition, i.e. a preparation wherein the amounts of either active agent remains constant for the entire at least 21-day period, or the amounts of either or both active agents may be varied over the at least 21-day period to generate a multiple-phase preparation, e.g. a two- or three-phase preparation, substantially as disclosed in, e.g., EP 148 724.

In an interesting embodiment of the present invention relating to the use of a medicament for inhibiting ovulation, the medicament is administered on each day of at least 21 consecutive days, a daily dosage unit comprising a combination of drospirenone in an amount of from about 2 mg to about 4 mg and ethinyl estradiol in an amount from about 0.01 to about 0.05 mg, followed by administering, on each day of 7 or less consecutive days, a daily dosage unit containing no active agent, or alternatively, administering no dosage units for 7 days or less.

In a further suitable embodiment, each of the daily dosage units comprising a combination of drospirenone and ethinyl estradiol are to be administered for 21, 22, 23 or 24 consecutive days, and each of the daily dosage units containing no active agent may be administered for 7, 6, 5 or 4 consecutive days, as appropriate. Furthermore, the daily dosage units comprising the combination of drospirenone and ethinyl estradiol may be administered for 28 consecutive days or 30 or 31 consecutive days. Suitably, the use of said medicament comprises administering, on each day of at least 21 consecutive days, a daily dosage unit comprising a combination of drospirenone in an amount of from about 2 mg to about 4 mg and ethinyl estradiol in an amount from about 0.01 to about 0.05 mg, followed by administering, on each day of 7 or less consecutive days, a daily dosage unit containing ethinyl estradiol alone in an amount of from about 0.01 mg to about 0.05 mg.

In this alternative method, the daily dosage units comprising the combination of drospirenone and ethinyl estradiol may suitably be administered for 21, 22, 23 or 24 consecutive days, and wherein the daily dosage units comprising ethinyl estradiol alone may then be administered for 7, 6, 5 or 4 consecutive days, as appropriate. In a further embodiment of the method, the daily dosage units comprising the combination of drospirenone and ethinyl estradiol are administered for 2–4, preferably 2 or 3, times 28 consecutive days, followed by administration of the daily dosage units comprising the combination of drospirenone and ethinyl estradiol for 21 consecutive days and subsequently administration of the daily dosage units comprising ethinyl estradiol alone for 7 consecutive days.

The entire disclosures of all applications, patents and publications, cited herein, and of U.S. Provisional Application Ser. No. 60/256,484, filed Dec. 20, 2000, and of EP Application No. 00610135.6, filed Dec. 20, 2000, are hereby incorporated by reference.

The present invention is further defined by the Examples.

BRIEF DESCRIPTION OF THE EXAMPLES

Example 1 discloses a pharmaceutical product according to some embodiments of the present invention along with pharmaceutical products known to the person skilled in the art. Table 1.3 illustrates the performance in terms of stability in comparison to known formulations after a fixed period of time under controlled environmental conditions. The data shows that direct compression of the powder blend results in good stability of ethinyl estradiol when provided in the form of a cyclodextrin complex (Product D). The product E was prepared to be polyvinylpyrrolidone-free according to the present invention. This product also shows good stability of the ethinyl estradiol in spite of being manufactured by granulation. However, in the case where the product includes polyvinylpyrrolidone and is manufactured according to Example 3 in U.S. Pat. No. 5,798,338 (Tablet A), the product is poorly stable.

Example 2 illustrates the stability of EE in Formulations D and E in comparison to other formulations in terms of the breakdown products isolated from samples upon storage after a fixed period of time under controlled environmental conditions.

Example 3 discloses the contents of one embodiment of the present invention, wherein the composition further comprises drospirenone.

Example 4 describes the morphology or some physical characteristics of a typical dosage form of a formulation according to the present invention.

Example 5 discloses a typical process for the preparation of a tablet.

Example 6 describes the method in which certain physical properties, namely the rate constant of the dissociation constant of the complex between EE and CD, was studied. The half-life of the 1:1 complex was determined to be 155.8 s and the dissociation constant was determined to be $4.45 \times 10^{-3}$ s$^{-1}$.

Example 7 describes the method in which the equilibrium stability constant (formation constant) of the complex between EE and CD was studied. The stability constant of the 1:1 complex was found to be $9.5 \times 10^{-4}$ M$^{-1}$. The solubility of complexed ethinyl estradiol was found to improve in comparison to the free steroid.

Example 8 describes the method in which the equilibrium stability constant (formation constant) of the complex between EE and CD in acidic medium was studied. The stability constant of the 1:1 and 1:2 complex in acidic medium is disclosed. The solubility of complexed ethinyl estradiol was found to improve in comparison to the free steroid in acidic medium.

Example 9 discloses the method in which the acid dissociation constant ($pK_a$) of the EE-CD complex in aqueous media was determined to be approx. 10.51 in comparison to the $pK_a$ of approx. 10.25 of the free steroid.

Example 10 describes the method in which the n-octanol/water partition coefficient of the EE-CD complex was determined and its dependence on pH. Its log P value ranges from 3.20 to 3.53.

Example 11 discussed whether the ethinyl estradiol-β-cyclodextrin complex can exist in multiple solid state forms and to provide test methods, which can detect and distinguish between such forms.

Example 12 describes typical preparations of an EE-CD complex.

EXAMPLES

The following examples are not a limitation on the invention. All temperatures are set forth uncorrected in degrees Celsius; and, unless otherwise indicated, all parts and percentages are by weight.

Example 1

Degradation of Ethinyl Estradiol in Various Formulations

Comparative stability data of five tablet formulations comprising ethinyl estradiol has been investigated. The various formulations differ from each other with respect to the manufacturing process, use of ethinyl estradiol in the form of a cyclodextrin complex and use of polyvinylpyrrolidone 25.000 (PVP). Tablet A was prepared as disclosed in U.S. Pat. No. 5,798,338, Example 3, such as by fluid bed granulation based on pre-mixing of active ingredient with lactose and no adjusting of the relative humidity of the granules. Tablets, B, C and E were prepared according to the manufacturing process disclosed herein.

TABLE 1.1

Summary of Parameters of Film-Coated Tablets

| Tablet | Manufacturing Process | Active agent | Excipient |
|---|---|---|---|
| A | fluid bed granulation* | EE-β-CD complex | +PVP |
| B | fluid bed granulation** | EE | +PVP |
| C | fluid bed granulation** | EE | |
| D | Direct compression | EE-β-CD complex | |
| E | fluid bed granulation** | EE-β-CD complex | |

*Fluid bed granulation as disclosed in Example 3 of U.S. Pat. No. 5,798,338,
**fluid bed granulation as disclosed in example 5 herein,
PVP = polyvinylpyrrolidone.

TABLE 1.2

Composition of Test Formulations

| | Tablets | | | | |
|---|---|---|---|---|---|
| Composition: | A | B | C | D | E |
| EE | — | ✓ | ✓ | — | — |
| EE-β-CD | ✓ | — | — | ✓ | ✓ |
| DRSP | — | ✓ | ✓ | ✓ | ✓ |
| Lactose | ✓ | ✓ | ✓ | ✓ | ✓ |
| maize starch | ✓ | ✓ | ✓ | ✓ | ✓ |
| micro cellulose | — | — | — | ✓ | — |
| starch 1500 | ✓ | ✓ | — | — | — |
| PVP 25.000 | ✓ | ✓ | — | — | — |
| Mg Stearate | ✓ | ✓ | ✓ | ✓ | ✓ |

Results

The content of ethinyl estradiol was determined by HPLC just after manufacturing (start) and following storage at various conditions for 3 and 12 months. The content of ethinyl estradiol is expressed relatively to the initial content of ethinyl estradiol that was added to each formulation.

TABLE 1.3

Content of ethinyl estradiol (% recovered)

| Formulation | start | 40° C., 75% RH | 60° C., 75% RH | 25° C., 60% RH | 40° C., 75% RH |
|---|---|---|---|---|---|
| | | | 3 months | 12 months | |
| A | 93.1 | 86.3 | 77.8 | 93.8 | 75.9 |
| B | 98.9 | 94.9 | 70.7 | 95.6 | 85.7 |
| C | 100.1 | 95.8 | 86.1 | 100.1 | 92.1 |
|   | 99.1 | 96.2 | 86.1 | 99.1 | 92.1 |
| D | 101.5 | 98.8 | 96.4 | 101.4 | 99.9 |
|   | 102.7 | 100.7 | 98.6 | 101.8 | 100.0 |
| E | 103.2 | 101.3 | 96.4 | 100.5 | 98.9 |
|   | 103.3 | 102.0 | 96.6 | 101.8 | 99.3 |

Example 2

Formation of Oxidative Degradation Products of Ethinyl Estradiol

The content of known oxidative degradation products of ethinyl estradiol was determined by HPLC following storage for 12 months at 25° C. and 60% relative humidity (RH) for 12 months. The molar content of each degradation products is expressed relatively to the initial molar content of ethinyl estradiol that was added to each formulation. Four formulations as well as the pure ethinyl estradiol and the ethinyl estradiol β-cyclodextrin complex were investigated.

TABLE 2.1

Stability results after 12 months, 25° C., 60% RH
Formation of degradation products (% of initial content of EE)

| Formulations | 6-α-OH-EE | 6-β-OH-EE | 6-Keto-EE | Δ9,11-EE | total known |
|---|---|---|---|---|---|
| EE | 0.004 | 0.005 | n.d | 0.38 | 0.389 |
| EE-β-CD | 0.002 | 0.003 | n.d | 0.38 | 0.385 |
| B | 0.04 | 0.07 | 0.32 | 0.74 | 1.20 |
| C | 0.05 | 0.09 | 0.11 | 0.73 | 1.00 |
|   | 0.04 | 0.07 | 0.08 | 0.70 | 0.91 |
| D | 0.01 | 0.02 | n.d | 0.49 | 0.52 |
|   | 0.01 | 0.01 | n.d | 0.45 | 0.47 |
| E | 0.03 | 0.01 | n.d | 0.46 | 0.50 |
|   | 0.02 | 0.01 | n.d | 0.40 | 0.43 | n.d = not detectable;
6-α-OH-EE = 6-α-hydroxy-ethinyl estradiol;
6-β-OH-EE = 6-β-hydroxy-ethinyl estradiol;
6-Keto-EE = 6-keto-ethinyl estradiol;
Δ9,11-EE = Δ9,11-ethinyl estradiol.

TABLE 2.2

Stability results after 12 months, 40° C., 75% RH
Formation of degradation products (% of initial content of EE)

| Formulations | 6-α-OH-EE | 6-β-OH-EE | 6-Keto-EE | Δ9,11-EE | total known |
|---|---|---|---|---|---|
| EE | 0.004 | 0.005 | n.d | 0.38 | 0.389 |
| EE-β-CD | 0.002 | 0.003 | n.d | 0.38 | 0.385 |
| B | 0.16 | 0.25 | 1.92 | 3.14 | 5.47 |
| C | 0.33 | 0.61 | 1.03 | 1.86 | 3.83 |
|   | 0.28 | 0.54 | 0.87 | 1.59 | 3.28 |
| D | 0.03 | 0.09 | 0.10 | 0.79 | 1.01 |
|   | 0.03 | 0.10 | 0.09 | 0.79 | 0.98 |

TABLE 2.2-continued

Stability results after 12 months, 40° C., 75% RH
Formation of degradation products (% of initial content of EE)

| Formulations | 6-α-OH-EE | 6-β-OH-EE | 6-Keto-EE | Δ9,11-EE | total known |
|---|---|---|---|---|---|
| E | 0.08 | 0.19 | 0.30 | 0.93 | 1.50 |
|   | 0.08 | 0.19 | 0.41 | 0.89 | 1.58 | n.d = not detectable;
6-α-OH-EE = 6-α-hydroxy-ethinyl estradiol;
6-β-OH-EE = 6-β-hydroxy-ethinyl estradiol;
6-Keto-EE = 6-keto-ethinyl estradiol;
Δ9,11-EE = Δ9,11-ethinyl estradiol.

Example 3

Typical compositions consisting of a tablet core is described. The tablet core may optionally be film-coated or sugar coated using the described ingredients. The specific ingredients are typical suitable ingredients according to the invention, but are not limited to those.

TABLE 3

| Ingredient | Specific ingredients | Amount % w/w |
|---|---|---|
| Tablet core: | | |
| Active agent I | estrogens in the form of an complex with a cyclodextrin | |
| Active agent II | a progestogen | |
| Filler | lactose, starch, cellulose | 0–95% |
| Binder | starch, cellulose, hydroxypropylcellulose, hydroxypropylmethylcellulose, maltodextrine | 0–15% |
| Glidant | colloidal silicon dioxide | 0–5% |
| Disintegrant | starch, carmellose-calcium, crosscarmellosesodium, carboxymethylstarch sodium | 0–15% |
| Stabilizer/antioxidant | tocopherole acetate, Propyl gallate, ascorbic acid, ascorbic palmitate | 0–5% |
| Lubricant | magnesium stearate | 0–5% |
| Film coating: | | |
| Film-binding agent | hydroxypropylmethylcellulose, polyacrylic acid derivatives, Eudragit | 20–100% |
| Plasticizer | polyethylene glycole | 0–20% |
| Filler | talc, titanium dioxide, calcium carbonate | 0–20% |
| Pigment | titanium dioxide, calcium carbonate | 0–20% |
| Colorant | ferric oxide pigments | 0–10% |
| Sugar coating | | |
| Coating agent | sucrose | 30–90% |
| Plasticizer | povidone 700000, polyethylene-glycol 6000 | 0–10% |
| Filler/coating agent: | talc, titanium dioxide, calcium carbonate | 10–50% |
| Humidifier | glycerol | 0–5% |
| Pigment | titanium dioxide, calcium carbonate | 0–10% |
| Colorant | ferric oxide pigments | 0–10% |
| Polishing agent | wax | 0–0.5% |

Example 4

Preferred Compositions

A preferred composition consists of the components listed below. The batch size is 200,000–550,000 tablets (development site) and 2.5 Mio tablets up to 5 Mio tablets (production site), respectively. Water is used as a processing aid for the manufacture of the tablet mass (fluid bed granulation) and the film-coating.

| Ingredient | One tablet (mg) | Development (kg) | Production (kg) |
|---|---|---|---|
| Drospirenone, micro 15 | 3.0 | 1.650 | 7.500 |
| Ethinyl estradiol-β-cyclodextrine complex, micro | 0.020 * | 0.011 * | 0.050 * |
| Lactose monohydrate | 48.18 | 26.499 | 120.450 |
| Corn starch | 28.0 | 15.400 | 70.000 |
| Magnesium stearate | 0.8 ** | 0.440 ** | 2.000 ** |
| tablet mass weight | 80.0 mg | 44.000 kg | 200.000 kg |
| hydroxypropylmethyl cellulose | 1.5168 | 0.83424 | 3.792 |
| Talc | 0.3036 | 0.16698 | 0.759 |
| titanium dioxide | 1.1748 | 0.64614 | 2.937 |
| ferric oxide pigment, red | 0.0048 | 0.00264 | 0.012 |
| weight of film-coat | 3.0 mg | 1.650 kg | 7.500 kg |
| total weight | 83.0 mg | 45.650 kg | 207.500 kg |

*: quantities given state the amount of ethinyl estradiol.

Example 5

Manufacturing Process

The manufacturing process comprises the following steps:
Prepare the granulation liquid: Suspend maize starch in purified water and add this suspension to purified water while stirring.
Prepare the granules: Introduce lactose, drospirenone micro 15, ethinyl estradiol-β-cyclodextrine complex micro and maize starch (portion) into the fluid bed granulator. Activate a continuous fluid bed and apply granulation liquid. Dry. Check relative humidity of the granulate mass. Dry the granulate mass if necessary until the desired range of relative humidity is reached (30%–45%).
Prepare the tablet mass: Introduce maize starch (portion) and magnesium stearate into the fluid bed granulator. Mix.
Compress the tablet mass Perform on a rotary tableting machine to tablet cores
Prepare the film-coating suspension: Suspend talc, ferric oxide pigment red and titanium dioxide in purified water and homogenise the suspension. Dissolve hydroxypropylmethyl cellulose in purified water while stirring. Combine and homogenise the mixture and check yield.
Film-coating: Introduce the tablet cores into a suitable coater and warm them up. Spray the appropriate amount of film-coating suspension continuously on the rotating cores while drying with warm air. Polish and check weight uniformity, disintegration time and yield.

Example 6

Dissociation of the EE-β-CD Complex

The rate constant of the dissociation constant of EE-β-CD complex in aqueous solution has been determined.

Test method

When dissolved in water, the ethinyl estradiol-β-Cyclodextrin complex dissociates into its components, ethinyl estradiol (EE) and the ligand β-Cyclodextrin (CD), following law of mass action equilibria.

1. $EE + CD \Leftrightarrow EE \cdot CD \qquad K_{11} = \frac{C_{EECD}}{C_{EE} \cdot C_{CD}}$ 2. $EE \cdot CD + CD \Leftrightarrow EE \cdot CD_2 \qquad K_{12} = \frac{C_{EECD_2}}{C_{EECD} \cdot C_{CD}}$ In this study, the dissociation rate of the 1:1 complex was determined using a stopped flow relaxation method with conductometric detection. An indirect method was applied based on a competition reaction using sodium-dodecylsulfate (SDS) which forms a complex as well. SDS as a salt is dissociated in aqueous solution and contributes sufficiently to. conductivity. When the $SD^-$ anion binds to β-Cyclodextrin, the complex formed will be less mobile as the free $SD^-$ ion in water and the electrical conductivity of the solution will decrease. The difference in conductivity of the free $DS^-$ anion and the complexed anion was used to detect the release kinetic of ethinyl estradiol from the clathrate complex with a stopped flow kinetic apparatus with conductivity detector.

Summary of Results

The dissociation rate constant of the Ethinyl estradiol-β-Cyclodextrin 1:1 complex was determined to be: $K^d = 4.45 \cdot 10^{-3}$ s$^{-1}$ Under first order conditions the half live of dissociation of the Ethinyl estradiol-β-Cyclodextrin 1:1 complex was calculated to be: $t_{1/2} = 155.8$ s (2.6 min)

Example 7

Stability Constant of the EE-β-CD Complex in Aqueous Solution

The Equilibrium Stability Constant (Formation Constant) of the EE-β-CD complex in aqueous solution was determined.

Background

The drug substance ethinyl estradiol-β-cyclodextrin complex is a clathrate complex containing one molecule Ethinyl estradiol and two molecules of β-cyclodextrin. The formation of the ethinyl estradiol-β-cyclodextrin clathrate in aqueous solution from its components ethinyl estradiol (S) and the ligand β-cyclodextrin (L) are defined by the following equations according to the law of mass action.

1. $S + L = SL \qquad K_{11} = \frac{C_{SL}}{C_S \cdot C_L}$

2. $SL + L = SL_2 \qquad K_{12} = \frac{C_{SL_2}}{C_{SL} \cdot C_L}$

The equilibrium stability constant (formation constants) $K_{11}$ was determined with a phase solubility technique. For $K_{12}$ only a rough estimation was obtained.

Summary of Results

The following data were obtained with the phase solubility diagram technique (PSD) in aqueous solutions at 20° C.

| | |
|---|---|
| Stability constant of the 1:1 complex: | $K_{11} = 9.5 \cdot 10^4 \, M^{-1}$ |
| Solubility of Ethinyl estradiol: | $S_{EE} = 2.17 \cdot 10^{-5}$ mol/l (6.43 $\cdot 10^{-3}$ g/l) |
| Solubility of the 1:1 complex: | $S_{11} = 1.92 \cdot 10^{-3}$ mol/l (2.75 g/l) |
| Solubility of the 1:2 complex: | $S_{12} = 1.44 \cdot 10^{-3}$ mol/l (3.7 g/l) |

Example 8

Stability Constant of the EE-β-CD Complex in 0.1 M HCl

The Equilibrium Stability Constant (Formation Constant) of the EE-β-CD complex in 0.1 M HCl was Determined as Described in Example 7.

Summary of Results

The following data were obtained with the phase solubility diagram technique (PSD) in 0.1 M HCl at 20° C.

| | |
|---|---|
| Stability constant of the 1:1 complex: | $K_{11} = 1.56 \cdot 10^4 \, M^{-1}$ |
| Overall stability constant of the 1:2 complex (= $K_{11} \cdot K_{12}$): | $K^*_{12}$ = approx. $1.6 \cdot 10^4 \, M^{-1}$ |
| Solubility of ethinyl estradiol: | $S_{EE} = 1.68 \cdot 10^{-4}$ mol/l (0.05 g/l) |
| Solubility of the 1:1 complex: | $S_{11} = 2 \cdot 10^{-3}$ mol/l (2.9 g/l) |
| Solubility of the 1:2 complex: | $S_{12} = 5 \cdot 10^{-4}$ mol/l (1.3 g/l) |

Example 9

Dissociation Constant of the EE-β-CD Complex in Aqueous Solution

The Acid Dissociation Constant of the EE-β-CD complex in aqueous media was determined.

Background

The drug substance ethinyl estradiol-β-cyclodextrin complex is a clathrate complex containing one molecule of ethinyl estradiol and two molecules of β-cyclodextrin. In aqueous solution, the ethinyl estradiol-β-cyclodextrin complex dissociates into its components according to the law of mass action. To restrain the dissociation of the ethinyl estradiol-β-cyclodextrin complex an aqueous solution containing an approx. 300 fold (0.0114 molar) excess of β-cyclodextrin over ethinyl estradiol was used in the measurements. The pKa was measured by a photometric titration method following the guidance given in the Environmental Assessment Technical Handbook.

Summary of Results

The acid dissociation constant of the ethinyl estradiol-β-cyclodextrin complex was determined at 20° C. to be:

$pK_a = 10.51 \pm 0.03$

For comparison the pKa of ethinyl estradiol in the absence of β-cyclodextrin is:

$pK_a = 10.25 \pm 0.04$

Example 10

Log P Value of the EE-β-CD Complex

Background

The drug substance, ethinyl estradiol-β-cyclodextrin complex, is a complex containing one molecule of ethinyl estradiol and two of molecules β-cyclodextrin.

The partition of the ethinyl estradiol-β-cyclodextrin complex is determined upon equilibration in a two-phase system, n-octanol/water. Only the total amount of ethinyl estradiol in the aqueous and the octanolic phase can be determined. The result is the apparent n-octanol/water partition coefficient of ethinyl estradiol. For determination of the pH dependence of the apparent n-octanol/water partition coefficient of ethinyl estradiol measurements were performed at pH 5, 7 and 9 with the flask-shaking method according to OECD guideline 107[1]). Measurements were performed with aqueous solutions buffered to pH 5, 7 and 9. The ethinyl estradiol concentration in each phase after equilibration at 25° C. was determined by HPLC.

Summary of Results

| | The pH dependence of the apparent partition coefficient of ethinyl estradiol | | |
|---|---|---|---|
| pH | mean app. $P_{OW}$ with standard deviations | app. log $P_{OW}$ | 95% confidence intervals for app. log $P_{OW}$ |
| 5 | 2395 ± 623 | 3.38 | 3.28–3.46 |
| 7 | 3424 ± 1298 | 3.53 | 3.35–3.67 |
| 9 | 1579 ± 505 | 3.20 | 3.08–3.29 |

Example 11

Solid State Forms of the Ethinyl Estradiol-β-cyclodextrin Complex

Multiple solid state forms of the ethinyl estradiol-β-cyclodextrin were determined, and test methods that can detect and distinguish between such forms were provided.

Background

A variety of crystallisation products obtained under different crystallisation, drying and storage conditions are investigated with respect to their solid state form. A selection of the following analytical methods is applied in order to identify and characterise solid state forms as deemed appropriate and possible:
X-ray powder diffraction (XRPD)
differential thermal analysis (DTA) in combination with thermogravimetry (TG)
differential scanning calorimetry (DSC) in combination with thermogravimetry (TG)

Summary of Results

Evidences of complex formation is obtained by investigation of pure ethinyl estradiol and beta-cyclodextrin, mechanical mixtures of both substances as well as samples of the ethinyl estradiol-beta-cyclodextrin complex with X-ray powder diffraction and thermal analysis. According to these investigations at least about 90% of the ethinyl estradiol should be bonded in the complex.

The prevalent form of the ethinyl estradiol-beta-cyclodextrin complex is that of a hydrate containing varying amounts of water. The variability of the water content is a consequence of an inherent property of free cyclodextrin as well as of its inclusion compounds (complexes or clathrates), the equilibration of at least part of the hydrate water with the ambient atmosphere. On storage, an equilibrium water content is established which depends on temperature, pressure and relative humidity. The hydrate water can be readily lost from the crystal lattice. Under more severe drying conditions all crystal water can be removed, however the resulting material is extremely hygroscopic and therefore not of relevance for the drug substance. The same applies to fully water-saturated hydrates, which is stable only in the presence of mother liquid or under relative humidity of more than 97%. Thus, any discussion on the solid state forms of the ethinyl estradiol-β-cyclodextrin complex has to concentrate on the characterisation of a range of hydrates having intermediate water contents with an upper limit at water saturation.

The hydrate water is a part of the crystal lattice and therefore alterations of the water content are connected with changes in the crystal lattice. This is manifested by differences in the X-ray powder pattern of batches of clathrate with varying water content. According to these patterns four different types can be distinguished. Batches of type I contain less than 1% water. In batches of types II and III between 4% and 10% water, and 8% and 15% water, respectively, are found. Type IV is characterised by a water content of more than 15%. However, there's no clear dividing line between two neighbouring types. The position of the diffraction peaks is changed gradual due to swelling and shrinking of the crystal lattice during water sorption or desorption. Investigations of the four types by differential thermal analysis in combination with thermogravimetry have shown that the dehydration takes place between 25° C. and 170° C.

The different forms are readily and reversibly interchanged by adjustment of the ambient humidity conditions. This behaviour indicates considerable rigidity of the structural framework which does not allow profound alteration of the basic arrangement of the beta-cyclodextrin/ethinyl estradiol building blocks of the solid during hydration and dehydration.

Example 12

Preparation of the Ethinyl Estradiol-beta-cyclodextrin Complex

The ethinyl estradiol-beta-cyclodextrin complex is obtained by co-precipitation as follows:

Process 1 (P1): Ethinyl estradiol is dissolved in ethanol. β-cyclodextrin is dissolved at 45° C. in water. The ethinyl estradiol solution is added to the β-cyclodextrin solution. The obtained suspension is stirred for some hours at 20 to 25° C. and afterwards at 2° C. The crystallization product is isolated and dried by methods described infra.

Process 2 (P2): Ethinyl estradiol is dissolved in acetone. β-cyclodextrin is dissolved at 45 C in water. The ethinyl estradiol solution is added to the beta-cyclodextrin solution. The obtained suspension is stirred for some hours at temperatures below 25° C. Afterwards, the crystallization product is isolated and dried by methods described infra.

The mechanical mixtures of β-cyclodextrin and ethinyl estradiol are prepared by weighing and afterwards homogenization by grinding in an agate mortar.

TABLE 12.1a

Crystallization products of the complex

| batch | solvent/treatment conditions | content of EE [%] | water content [%] |
|---|---|---|---|
| Im2180 | P 1, dried in a vacuum drying cabinet | 10.9 | 5.57 |
| Im2181 | P 1, dried in a vacuum drying cabinet | 11.2 | 5.26 |
| Im2182/1 | P 1, dried 1 h at r.t. over $P_2O_5$ in a vacuum desiccator | n.d. | 6.5 |
| Im2182/2 | P 1, dried 2 h at r.t. over $P_2O_5$ in a vacuum desiccator | n.d. | 6.5 |
| Im2182/3 | P 1, dried 4 h at r.t. over $P_2O_5$ in a vacuum desiccator | n.d. | 6.4 |
| Im2182/4 | P 1, dried 4 h at r.t. over $P_2O_5$ in a vacuum desiccator | n.d. | 7.7 |
| Im2182/5 | P 1, dried 43.5 h at r.t. over $P_2O_5$ in a vacuum desiccator | 10.8 | 4.47 |
| Im2182/6 Act. | P 1, washed with acetone, dried 3 h at 2° C. over $P_2O_5$ in a vacuum desiccator | 10.9 | 4.65 |
| Im2182/7 | P 1, washed with acetone and water, dried 3 h at 2° C. over $P_2O_5$ in a vacuum desiccator | 10.6 | 4.47 |
| Im2183/V | P 1, dried some hours at r.t. over $P_2O_5$ in a vacuum desiccator | 11.4 | 4.21 |
| Im2183/VT | P 1, dried in a vacuum drying cabinet | 10.7 | 5.59 |
| Im2183/L | P 1, stored at air | 11.4 | 10.2 |
| Im2183/VT + L | P 1, dried in a vacuum drying cabinet and than storage at air | 10.6 | 8.75 |
| Im2184 | P 1, dried in a vacuum drying cabinet | 10.9 | 5.60 |
| Im2188 | P 1, 20 h at r.t. | 10.8 | 11.85 |
| Im2190f. | P 1, dried in a vacuum drying cabinet - 1 d | n.d. | — |
| Im2191f. | P 1, dried in a vacuum drying cabinet - 1 d | n.d. | — |
| Im2190 | P 1, dried in a vacuum drying cabinet - 5 d | 10.6 | 7.5 |
| Im2191 | P 1, dried in a vacuum drying cabinet - 5 d | 10.6 | 7.7 |
| 28052591 | batch Im2190 micronized | 10.7 | 8.23 |
| Im2220 | P 2, dried in a vacuum drying cabinet | 10.7 | 5.61 |
| Im2221 | P 1, dried in a vacuum drying cabinet | 10.2 | 5.78 |
| Im2222 | P 1, dried in a vacuum drying cabinet | 10.4 | 5.57 |
| Im2223 | P 1, dried in a vacuum drying cabinet | 10.1 | 5.64 |
| Im2224 | P 2, dried in a vacuum drying cabinet | 10.4 | 5.75 |

TABLE 12.1b

Crystallization products of the complex

| Batch | solvent/treatment conditions | content of EE [%] | water content [%] |
|---|---|---|---|
| Im2225/1 | P 1; washed 2 × water; dried in a vacuum drying cabinet | 11.2 | 3.34 |
| Im2225/2 | P 1; washed 2 × water, 1 × acetone; dried in a vacuum drying cabinet | 10.5 | 3.31 |

TABLE 12.1b-continued

Crystallization products of the complex

| Batch | solvent/treatment conditions | content of EE [%] | water content [%] |
|---|---|---|---|
| Im2225/3 | P 1; washed 2 × water, 1 × acetone, 1 × water; dried in a vacuum drying cabinet | 10.9 | 3.8 |
| Im2230 | P 1; washed 1 × water, 1 × acetone, 1 × water; dried in a vacuum drying cabinet | 10.8 | 4.35 |
| Im2231 | P 1; washed 1 × water, 1 × acetone, 1 × water; dried in a vacuum drying cabinet | 11 | 2.63 |
| Im2240 | P 1; washed 1 × water, 1 × acetone, 1 × water; dried in a vacuum drying cabinet | 10.5 | 6.71 |
| 28052591, DVS1 0% RH | batch 28052591 after one sorption/desorption cycle, stored at 0% RH | n.d. | <1%[5] |
| Im2180, DVS1 0% RH | batch Im2180 after sorption/desorption cycle, stored at 0% RH | n.d. | <1%[5] |
| Im2180, DVS1 45% RH | batch Im2180 stored at 45% RH | n.d. | 6.5[5] |
| Im2180, DVS1 70% RH | batch Im2180 stored at 70% RH | n.d. | 9.5[5] |
| Im2180, DVS1 75% RH | batch Im2180 stored at 75% RH | n.d. | 9.5[5] |
| Im2180, DVS1 93% RH | batch Im2180 stored at 93% RH | n.d. | ~15[5] |
| Im2180, 3 d Mg(ClO$_4$)$_2$ | batch Im2180 stored 3 d over Mg(ClO$_4$)$_2$ | n.d. | n.d. |
| Im2190, 5 d 97% RH | batch Im2190 stored 5 d at 97% RH | n.d. | ~16.7[5] |
| Im2190, 7 d 97% RH | batch Im2190 stored 7 d at 97% RH | n.d. | ~16.5[5] |
| 28052591, 7 d Mg(ClO$_4$)$_2$ | batch 28052591 stored 7 d over Mg(ClO$_4$)$_2$ | n.d. | <0.1[5] |
| 28052591, 7 d 97% RH | batch 28052591 stored 7 d at 97% RH | n.d. | 16.9[5] |
| 28052591, wet | batch 28052591 suspended in water, no drying | — | — |
| 28052591, 7 d 75% RH | batch 28052591 stores 7 d at 75% RH | n.d. | 10.5[5] |

[5]calculated from the water content of the starting material and the observed mass change The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for inhibiting ovulation in a female comprising administering to the female a composition comprising:
   i) a complex between an estrogen and a cyclodextrin;
   ii) drospirenone; and
   iii) one or more excipients,
   the composition having a stability such that said estrogen is in amount of at least 85% w/w in relation to the initial content of said estrogen after storage for 12 months at 40° C. and 75% relative humidity (RH).

2. The method of claim 1, wherein the complex between an estrogen and a cyclodextrin is a granulate preparation having a relative humidity of at most 60%, as determined at a temperature between 20° C. and 40° C.

3. The method of claim 1, wherein the estrogen is in an amount corresponding to a therapeutically equivalent amount of ethinyl estradiol of from about 0.002% w/w to 2% w/w, based on the total composition.

4. The method of claim 1, wherein the estrogen is in an amount from about 0.002% w/w to 2% w/w, based on the total composition.

5. The method of claim 1, wherein the estrogen is in an amount from about 0.004% w/w to 0.2% w/w, based on the total composition.

6. The method of claim 1, wherein the estrogen is ethinyl estradiol and the cyclodextrin is β-cyclodextrin, and the ethinyl estradiol is in an amount relative to the ethinyl-estradiol-β-cyclodextrin complex of from about 5% w/w to 20% w/w.

7. The method of claim 1, wherein the estrogen is ethinyl estradiol and the cyclodextrin is β-cyclodextrin, and the ethinyl estradiol is in an amount relative to the ethinyl-estradiol-β-cyclodextrin complex of from about 8% w/w to 15% w/w.

8. The method of claim 1, wherein the amount of drospirenone is from about 0.4% to 20% w/w.

9. The method of claim 1, wherein the amount of drospirenone is from about 0.8% w/w to 10% w/w, based on the total composition.

10. The method of claim 1, wherein the amount of drospirenone is from about 1.5% w/w to 5% w/w, based on the total composition.

11. The method of claim 1, wherein the one or more excipients comprises polyvinylpyrrolidone in an amount of at most 2% w/w.

12. The method according to claim 1, wherein the one or more excipients comprises polyvinylpyrrolidone in an amount of at most 1% w/w.

13. The method according to claim 1, wherein the one or more excipients comprises polyvinylpyrrolidone in ah amount of at most 0.5% w/w.

14. The method according to claim 1, wherein the one or more excipients comprises polyvinylpyrrolidone in an amount of at most 0.2% w/w.

15. The method according to claim 1, wherein the composition is essentially free of polyvinylpyrrolidone.

16. The method according to claim 1, wherein the composition comprises one or more excipient(s) which is/are selected from the group consisting of starch, cellulose, hydroxypropylcellulose, hydroxypropylmethylcellulose and maltodextrin.

17. The method according to claim 1, wherein the estrogen in the composition is selected from the group consisting of ethinyl estradiol, estradiol, estradiol sulfamates, estradiol valerate, estradiol benzoate, estrone, estrone sulfate and mixtures thereof.

18. The method according to claim 1, wherein the estrogen is ethinyl estradiol.

19. The method according to claim 1, wherein the cyclodextrin is selected from the group consisting of α-cyclodextrin, β-cyclodextrin, γ-cyclodextrin and alkylated or acylated derivatives thereof.

20. The method according to claim 1, wherein the cyclodextrin is β-cyclodextrin or an alkylated or acylated derivative thereof.

21. The method according to claim 1, wherein the estrogen is in an amount relative to the cyclodextrin such that a molar ratio between the estrogen and the cyclodextrin is from about 2:1 to 1:10.

22. The method according to claim 1, wherein the drospirenone is in micronized form.

23. The method according to claim 1, wherein the complex between an estrogen and a cyclodextrin is micronized.

24. The method according to claim 1, wherein the composition further comprises an antioxidant.

25. The method according to claim 1, wherein the granulated preparation has a mean particle size of at least about 100 μm.

26. The method of claim 1, wherein the composition has a stability such that said estrogen is in an amount of at least 90% w/w in relation to the initial content of said estrogen after storage for 12 months at 40° C. and 75% relative humidity (RH).

27. A method for hormone replacement therapy in a female comprising administering to the female a composition comprising:
   i) a complex between an estrogen and a cyclodextrin;
   ii) drospirenone; and
   iii) one or more excipients,
   the composition having a stability such that said estrogen is in amount of at least 85% w/w in relation to the initial content of said estrogen after storage for 12 months at 40° C. and 75% relative humidity (RH).

28. The method of claim 27, wherein the complex between an estrogen and a cyclodextrin is a granulate preparation having a relative humidity of at most 60%, as determined at a temperature between 20° C. and 40° C.

29. The method of claim 27, wherein the estrogen is in an amount corresponding to a therapeutically equivalent amount of ethinyl estradiol of from about 0.002% w/w to 2% w/w, based on the total composition.

30. The method of claim 27, wherein the estrogen is in an amount from about 0.002% w/w to 2% w/w, based on the total composition.

31. The method of claim 27, wherein the estrogen is in an amount from about 0.004% w/w to 0.2% w/w, based on the total composition.

32. The method of claim 27, wherein the estrogen is ethinyl estradiol and the cyclodextrin is β-cyclodextrin, and the ethinyl estradiol is in an amount relative to the ethinyl-estradiol-β-cyclodextrin complex of from about 5% w/w to 20% w/w.

33. The method of claim 27, wherein the estrogen is ethinyl estradiol and the cyclodextrin is β-cyclodextrin, and the ethinyl estradiol is in an amount relative to the ethinyl-estradiol-β-cyclodextrin complex of from about 8% w/w to 15% w/w.

34. The method of claim 27, wherein the amount of drospirenone is from about 0.4% to 20% w/w.

35. The method of claim 27, wherein the amount of drospirenone is from about 0.8% w/w to 10% w/w, based on the total composition.

36. The method of claim 27, wherein the amount of drospirenone is from about 1.5% w/w to 5% w/w, based on the total composition.

37. The method of claim 27, wherein the one or more excipients comprises polyvinylpyrrolidone in an amount of at most 2% w/w.

38. The method according to claim 27, wherein the one or more excipients comprises polyvinylpyrrolidone in an amount of at most 1% w/w.

39. The method according to claim 27, wherein the one or more excipients comprises polyvinylpyrrolidone in an amount of at most 0.5% w/w.

40. The method according to claim 27, wherein the one or more excipients comprises polyvinylpyrrolidone in an amount of at most 0.2% w/w.

41. The method according to claim 27, wherein the composition is essentially free of polyvinylpyrrolidone.

42. The method according to claim 27, wherein the composition comprises one or more excipient(s) which is/are selected from the group consisting of starch, cellulose, hydroxypropylcellulose, hydroxypropylmethylcellulose and maltodextrin.

43. The method according to claim 27, wherein the estrogen in the composition is selected from the group consisting of ethinyl estradiol, estradiol, estradiol sulfamates, estradiol valerate, estradiol benzoate, estrone, estrone sulfate and mixtures thereof.

44. The method according to claim 27, wherein the estrogen is ethinyl estradiol.

45. The method according to claim 27, wherein the cyclodextrin is selected from the group consisting of α-cyclodextrin, β-cyclodextrin, γ-cyclodextrin and alkylated or acylated derivatives thereof.

46. The method according to claim 27, wherein the cyclodextrin is β-cyclodextrin or an alkylated or acylated derivative thereof.

47. The method according to claim 27, wherein the estrogen is in an amount relative to the cyclodextrin such that a molar ratio between the estrogen and the cyclodextrin is from about 2:1 to 1:10.

48. The method according to claim 27, wherein the drospirenone is in micronized form.

49. The method according to claim 27, wherein the complex between an estrogen and a cyclodextrin is micronized.

50. The method according to claim 27, wherein the composition further comprises an antioxidant.

51. The method according to claim 27, wherein the granulated preparation has a mean particle size of at least about 100 μm.

52. The method of claim 27, wherein the composition has a stability such that said estrogen is in an amount of at least 90% w/w in relation to the initial content of said estrogen after storage for 12 months at 40° C. and 75% relative humidity (RH).

* * * * *